US00PP37588P2

(12) United States Plant Patent
Byrne et al.

(10) Patent No.: US PP37,588 P2
(45) Date of Patent: Aug. 18, 2026

(54) NECTARINE TREE NAMED 'TX2B444LWN'

(50) Latin Name: *Prunus persica.*
Varietal Denomination: TX2B444LWN

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 19/336,355

(22) Filed: Sep. 22, 2025

(51) Int. Cl.
*A01H 6/74* (2018.01)

(52) U.S. Cl.
USPC ..... Plt./188
CPC ..... *A01H 6/7454* (2018.05)

(58) Field of Classification Search
USPC ..... Plt./188
CPC ..... A01H 5/0856
See application file for complete search history.

(56) References Cited

U.S. PATENT DOCUMENTS

| | | | |
|---|---|---|---|
| PP14,627 | P3 | 3/2004 | Byrne et al. |
| PP14,629 | P3 | 3/2004 | Byrne et al. |
| PP28,077 | P3 | 6/2017 | Byrne et al. |

OTHER PUBLICATIONS

U.S. Appl. No. 19/336,292, filed Sep. 22, 2025, Byrne et al.
Andersen and Sherman, 1995. SuncoastNectarine. HortScience 30(2):383-384.

*Primary Examiner* — Kent L Bell
(74) *Attorney, Agent, or Firm* — Dentons US LLP

(57) ABSTRACT

Disclosed is a new variety of as a variety of *Prunus persica* named 'TX2B444LWN', which requires approximately 450 chilling units of dormancy, produces subacid, white-fleshed firm clingstone nectarine fruit with a 80-90% maroon blush over an ivory ground color that matures early in the season.

5 Drawing Sheets

Latin name of the genus and species of the plant claimed: *Prunus persica.*

Variety denomination: 'TX2B444LWN'.

BACKGROUND OF THE INVENTION

This invention relates to a nectarine tree and, more specifically, to a nectarine tree referred to as a variety of *Prunus persica* named 'TX2B444LWN', which requires approximately 450 chilling units of dormancy, produces a subacid, white-fleshed firm clingstone nectarine with a 80-90% maroon blush over an ivory ground color that matures early in the season. The present nectarine tree was the result of an ongoing Stone Fruit Breeding Program in College Station, Brazos County, Texas. To this end, controlled crosses were made each year to produce seedling populations from which improved progenies are evaluated and selected. The seedling 'TX2B444LWN' was from a cross between the high acid white-fleshed nectarine selection 'TX3B101WN' (not patented) and the subacid, white-fleshed nectarine 'Smooth Delight One'. 'TX3B101WN' was a selection from a hybrid population derived from a cross between the low chill, yellow-fleshed nectarine 'Suncoast' (Andersen, P.C. and W.B. Sherman. 1995. 'Suncoast' nectarine. HortScience 30(2):383-384, not patented) and high-chill, white-fleshed nectarine 'Snow Queen' (U.S. Plant Pat. No. 3733, 1975). The seed from this cross were planted in 2010 in College Station, TX. 'TX2B444LWN' was marked for subsequent observation in 2012 and noted as having exceptional characteristics. Two-year and older trees of the variety were subsequently evaluated in Fairfield (2016-2018) and Somerville (2016-2023), Texas.

'TX2B444LWN' was bud grafted onto virus-free 'Nemaguard' (not patented, The Brooks and Olmo Register of Fruit and Nut Varieties, 3rd Ed., American Society of Horticultural Science Press, Alexandria, VA, 1997) peach rootstock at the nursery site in Oakdale, CA. The variety was subsequently planted at experimental orchards at three sites in Texas (Pleasanton, Somerville, and Fairfield). Fruit from the resulting propagation has been evaluated during the period from 2016 to 2023 fruit seasons. This evaluation clearly demonstrated that the re-propagated trees were true to the characteristics of the original seedling in all observable aspects.

SUMMARY OF THE INVENTION

The 'TX2B444LWN' nectarine produces glabrous fruit that ripens in the early season; is firm and has a 80-90% maroon blush over an ivory ground color. In this regard, the present variety of nectarine tree bears fruit that ripen for commercial harvesting and shipment in early May to mid-May, when the fruit is grown in the medium chill zone of Texas. 'TX2B444LWN' ripens about one week earlier than its female parent, the nectarine selection 'TX3B101WN' (not patented) and with its pollen parent 'Smooth Delight One' (patented, U.S. Plant Pat. No. 28,077). It blooms about two weeks before its female parent and a few days after its pollen parent. 'TX2B444LWN' differs from its female parent as it requires 200 hours less chill hours accumulation to fruit, ripens about one week earlier and has subacid fruit as compared to the high acid fruit of the selection 'TX3B101WN'. 'TX2B444LWN' differs from its pollen parent as it blooms 2-3 days after and has non showy flowers as compared to the showy flowers of 'Smooth Delight One'.

'TX2B444LWN' differs from 'Smooth Delight Two' (patented, U.S. Plant Pat. No. 28,443) as 'TX2B444LWN' has non showy versus showy blooms, has white flesh versus yellow flesh, requires 50-100 more chill hours to fruit properly, and blooms 3 days later than 'Smooth Delight Two'. It differs from 'Smooth Delight Three' (patented, U.S. Plant Pat. No. 30,122P3) as 'TX2B444LWN' has non showy versus showy blooms, requires about 100 fewer chill hours to fruit properly, and blooms 5-6 days earlier than 'Smooth Delight Three'. Additionally, the new variety exhibits the potential to be commercialized in regions that have chilling accumulations that are relatively low.

BRIEF DESCRIPTION OF THE DRAWINGS

This new variety of nectarine tree is illustrated by the accompanying photographs of 3-year old to 5-year old trees grown in Fairfield and Somerville, Texas, as provided in FIGS. 1-5.

These photographs show the plant's typical fruit, foliage, and flowers, and the colors shown are as true as can be reasonably obtained by conventional photographic procedures.

DETAILED BOTANICAL DESCRIPTION

Figure 1:
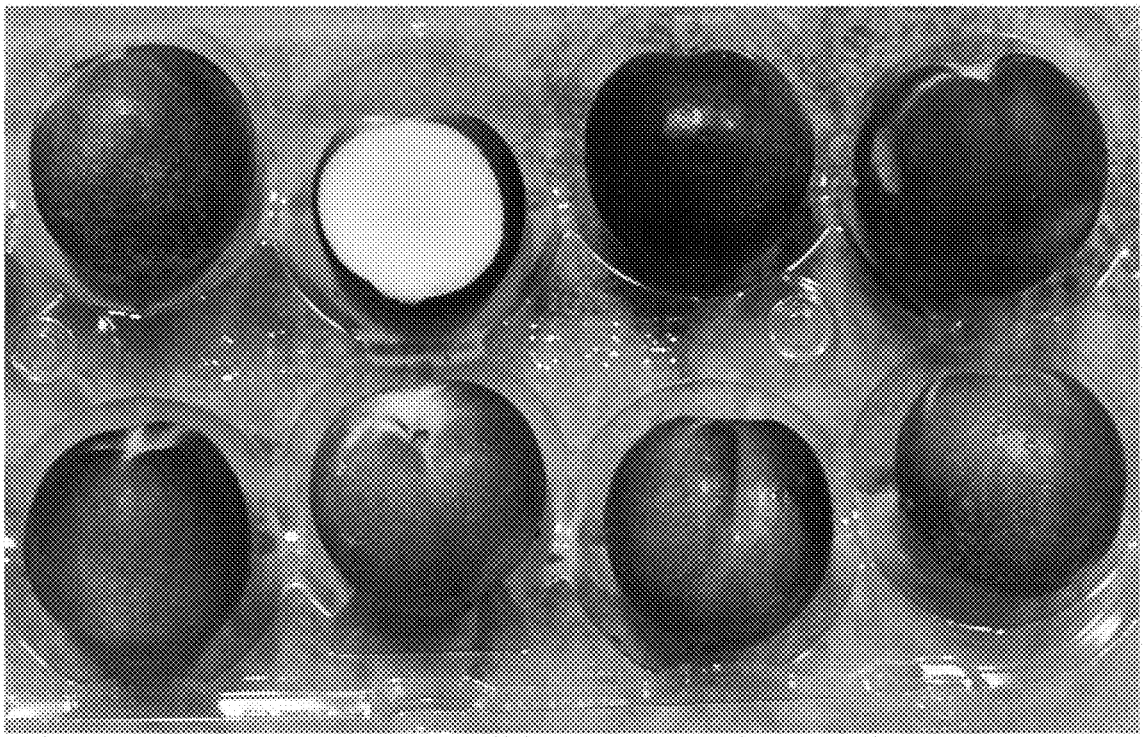
FIG. 1. Fruit of 'TX2B444LWN' produced in Fairfield, Texas showing external and internal coloration.
Figure 2:
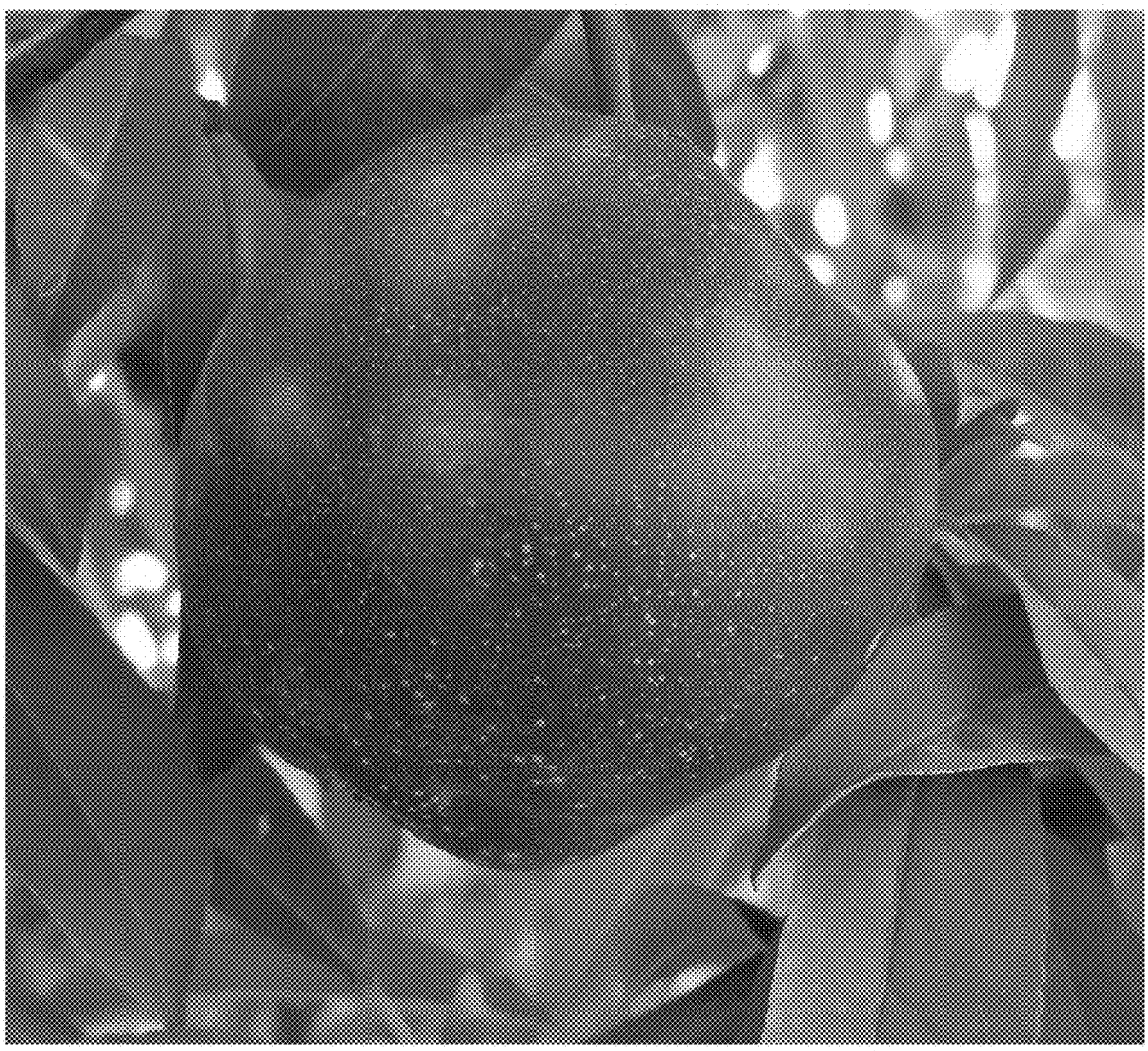
FIG. 2. 'TX2B444LWN' fruit produced in Somerville, Texas.
Figure 3:
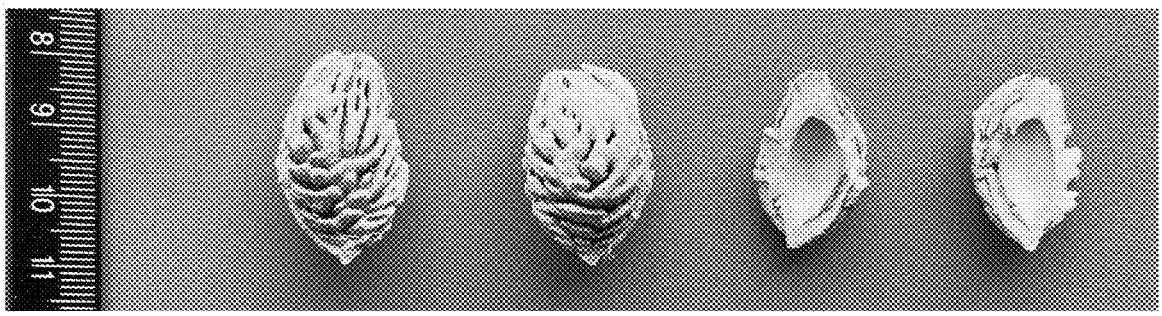
FIG. 3. Photograph of the endocarps of 'TX2B444LWN' nectarine. The ruler is in centimeters.
Figure 4:
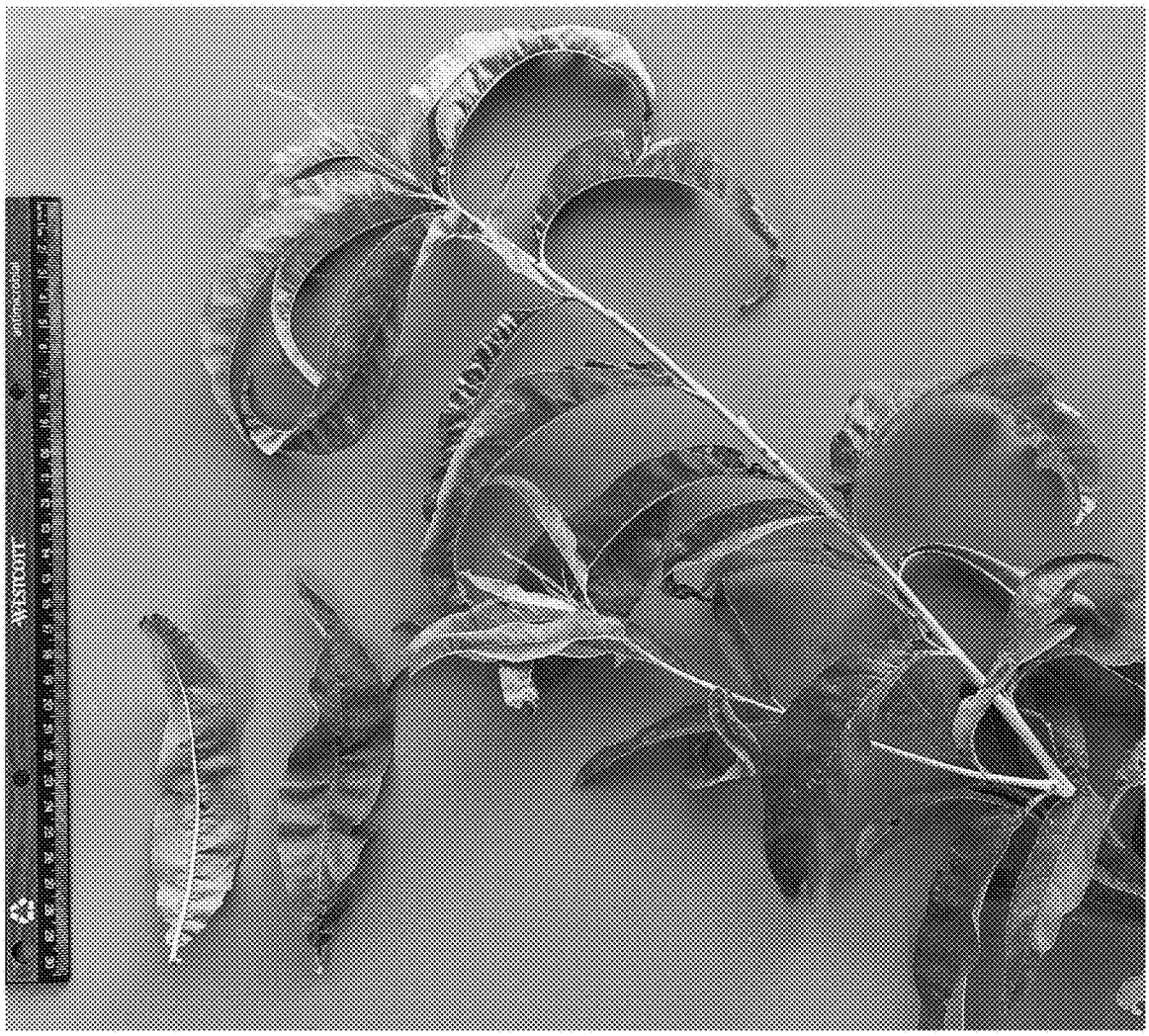
FIG. 4. A stem showing the leaves of 'TX2B444LWN' nectarine. The ruler is in centimeters.
Figure 5:
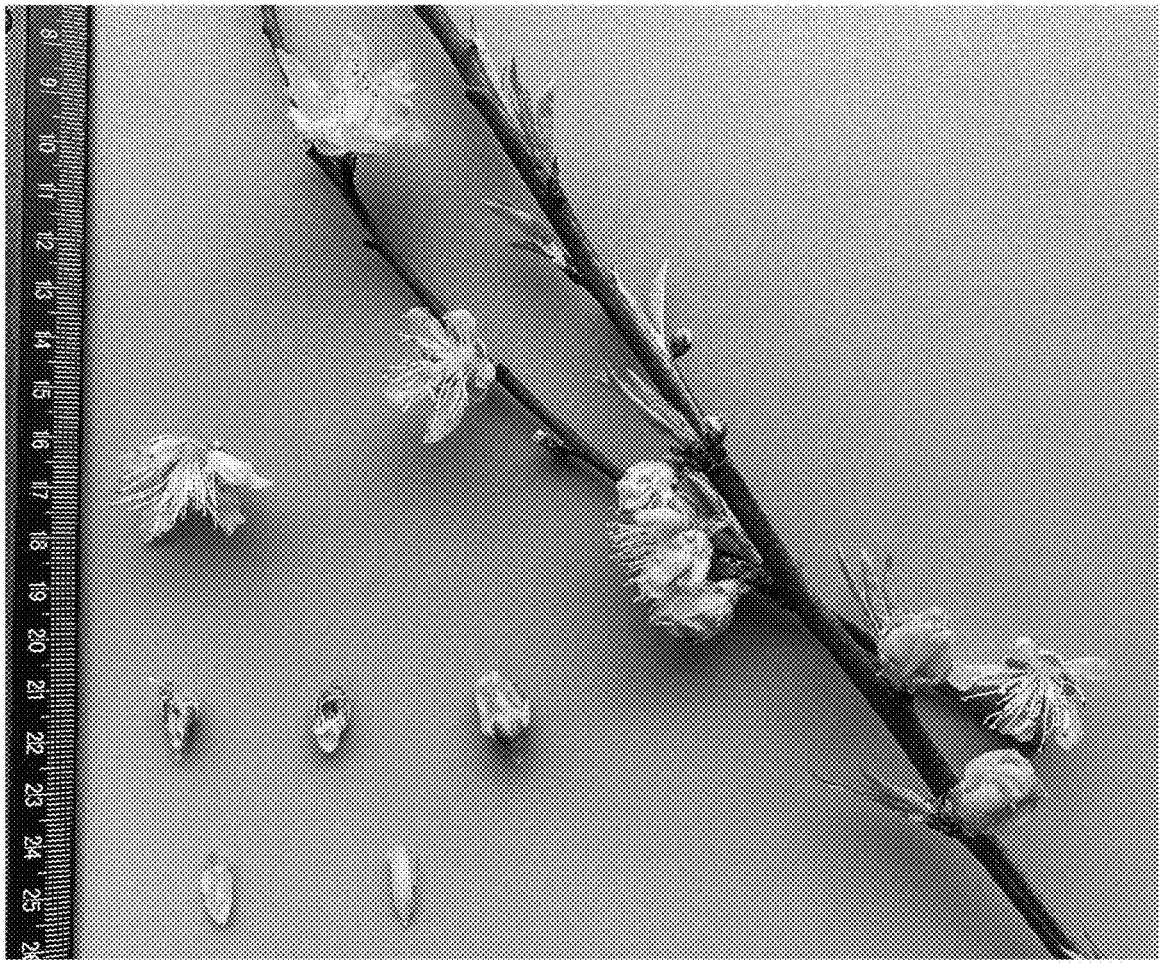
FIG. 5. A stem showing the flowers of 'TX2B444LWN' nectarine. The ruler is in centimeters.

Referring more specifically to the pomological details of this new and distinct variety of nectarine tree, the following has been observed under the ecological conditions prevailing at the experimental orchards in the medium chill zone of Texas (Fairfield and College Station). All major color code designations are by reference to The R.H.S. Colour Chart (2001 Edition) or the R.H.S. Mini Colour Chart (2005 Edition) provided by The Royal Horticultural Society of Great Britain. Colors are approximate as color depends on horticultural practices such as light level and fertilization rate, among others.

Tree:

*Size.*—Generally average to above average as compared to common peach and nectarine cultivars ripening in the early season of maturity.

*Height.*—9 feet (2.7 m) at the end of the 2024 growing season.

*Width.*—9 feet width (2.7 m) at the end of the 2024 growing season.

*Productivity.*—Produces annually in the medium chill zone of Texas without alternate bearing if temperatures of 28° F. or lower are not experienced during bloom. Trees are self-fertile and must be fruit thinned most years to avoid limb breakage and obtain optimal fruit size. The recommended fruit spacing for early to mid-season ripening fresh market peach cultivars for a full crop is one fruit every 6-8" of one-year old fruiting wood. Trees often set more fruit than needed for a full crop.

*Shape.*—The 'TX2B444LWN' nectarine has been trained in an open center configuration but exhibits a semi spreading growth type as seen in peach varieties 'Texprince' (patented, U.S. Plant Pat. No. 14,629) and 'Texking' (patented, U.S. Plant Pat. No. 14,627).

*Current Season Growth.*—The current season growth for the new variety was approximately 1 to 3 feet (0.3-0.9 m). Medium vigor as compared to other commercial cultivars in the medium chill zone of Texas. Regularity of Bearing — Regular in the absence of temperatures of 28° F. or below during bloom and considered hardy in the medium chill zone of Texas.

Trunk:

*Size.*—Approximately 4.25 inches (10.8 cm) in diameter and 13.5 inches (34.3 cm) in circumference when measured at a distance of approximately 12 inches (30.5 cm) above the soil level, at the end of the 2024 growing season on a three-year old tree.

*Bark Texture.*—Considered moderately rough with numerous folds of papery scarf-like skin being present. Bark Coloration — Variable, colors (R.H.S. colors) present are 156D of the Greyed-White Group, 166A, 175A and 176A of the Greyed-Orange Group and N200D of the Brown Group.

Branches:

*Size.*—Considered medium to moderately large for the species.

*Thickness.*—Average (about 3.9 to 5.2 cm in diameter as measured 10 cm from the trunk on a three-year old tree) as compared to other varieties.

*Surface Texture.*—Average and appearing furrowed on wood that is several years old.

*Lenticels.*—Numerous flat, oval lenticels present. The lenticels range in size from approximately 7 to 13 mm in width and were approximately 2 to 3 mm in height.

*Current Season Shoots.*—Surface texture-Substantially glabrous.

*Internode Length.*—Approximately 1.7 to 2.1 cm as measured in the middle of a current season stem. Color of Mature Branches — The predominant color (RHS2001) is 156D of the Greyed-White Group, 166A, 166B, 174A, 175A and 177A of the Greyed-Orange Group and N200D of the Brown Group.

Leaves:

*Size.*—Considered moderately large for the species. Leaf measurements have been taken from vigorous upright current season growth approximately at mid-shoot.

*Leaf Length.*—Approximately 161 to 171 mm.

*Leaf Width.*—*Approximately* 39 to 41 mm.

*Leaf Thickness.*—Less than 1 mm.

*Leaf Form.*—Lanceolate.

*Leaf Tip Form.*—Acuminate.

*Leaf Upper Surface Color* (*RHS*2001).—Green, 137A, 137B, 137C and 138A of the Green Group.

*Leaf Lower Surface Color* (*RHS*2001).—Green, 146A, 146B and 147B of the Yellow- Green Group.

*Leaf Lower Mid-Vein Color* (*RHS*2001).—Light yellow green, 145C and 145D of the Yellow-Green Group.

*Leaf Margins.*—Form — Considered crenate. Uniformity — Considered generally uniform.

*Leaf Petioles.*—Length — Approximately 11 to 14 mm. Thickness — Approximately 1.5 to 2 mm. Texture — Glabrous Color (RHS2001) — Pale green, 145C and 145D of the Yellow-Green Group.

*Leaf Glands.*—Size — Approximately 1 to 2 mm in height and 1 mm in width. Number — Generally 2 to 3 per leaf. Type — Reniform. Color (RHS2001) —Brown, 166A, 165A and 177A of the Greyed-Orange Group, N199B of the Grey-Brown Group and 200B and 200C of the Brown Group.

*Leaf Stipules.*—Length — Approximately 9 to 11 mm. Form — Lanceolate. Color (RHS2001) — Green, N144C, 145A and 151A of the Yellow-Green Group with red tips, 166A and 172A of the Greyed-Orange Group when young. Color is similar on both surfaces. The stipules are early deciduous. Ratio of wood (leaf) buds to flowering buds —Generally 2 flower buds per vegetative bud.

Flowers:

*Floral Buds.*—General — The floral buds are considered to be conic in form, and slightly appressed relative to the bearing shoot. Color — Mature flower buds are gray-brown, (approximately 165A, 166A and 177A of the Greyed-Orange Group, 197A, 197B, 198A and 198B of the Greyed-Green Group, 199A and 199B of the Grey-Brown Group and 200A, 200B and 200C of the Brown Group. The buds are considered hardy in the medium chill zone of Texas. Mature Bud Length — Approximately 5 to 6 mm. Mature Bud Width — Approximately 1 to 2 mm.

*Blooming Type.*—Mean date of full bloom in the medium chill zone of Texas was in mid-February (February 18$^{th}$ at Somerville and February 15$^{th}$ at Fairfield experimental plot), a few days before or with the commercial cultivars 'Texking' and 'Flordaking' (not patented, Andrews, C.P. 1979. 'Flordaking' peach. HortScience 14(1):81-82).

*Flower Type.*—Non-showy.

*Flower Size.*—Flower diameter at full bloom is approximately 23 to 26 mm.

*Bloom Quantity.*—Considered abundant.

*Flower Bud Frequency.*—Generally 2 per node.

*Petal Size.*—Width — Approximately 7 mm. Length —Approximately 10 to 12 mm.

*Petal Form.*—Broadly ovate.

*Petal Count.*—Nearly always 5.

*Petal Color* (*RHS*2001) *Abaxial/adaxial.*—Dark pink when young (68A, 68B and 73A of the Red-Purple Group), becoming darker near the petal claw.

*Petal Claw.*—Form — The claw is considered truncate in shape. Length — Approximately 1 mm. Width — Approximately 1 mm.

*Petal Margins.*—Generally considered variable, from nearly smooth to slightly undulate.

*Petal Apex.*—Generally —The petal apices appear slightly rounded.

*Flower Pedicel.*—Length — Average length of 2 to 5 mm. Thickness — Approximately 1 mm. Color (RHS2001) — A light green (144B, 144C, 144D, 145A and 145B of the Yellow-Green Group).

*Floral Nectaries.*—Color — Light to medium yellow (2A, 2B, 3B, 3C, 4A, 4B and 4C of the Yellow Group).

*Sepals.*—

*Sepal number.*—Five per flower. Surface Texture — The surface has a short, fine, wooly texture. Size —Average Height — 5.0 mm, Width — 2.5 mm. Form — Ovate Color (RHS2001) — Maroon and green with white (approximately 58A, 59C, 60A, 60B and 61A of the Red-Purple Group; N144A, N144B, 144C and 145A of the Yellow-Green Group and 155A, 155B, 155C, 155D of the White Group).

*Floral cup* (*hypanthium*).—Surface Texture — Generally glabrous. Color (RHS2001) — Maroon with green (approximately 58A, 59C, 60A, 60B and 61A of the Red-Purple Group and N144A, N144B, N144C and 145A of the Yellow-Green Group).

*Anthers.*—Color (RHS2001) — Dark orange (approximately N30A, N30B, N30C, N30D, 33A, 33B and 34A of the Orange-Red Group).

*Pollen Production.*—Pollen is abundant and is medium yellow in color (approximately 2A, 2B, 3A, 3B, 3C, 4A, 4B and 5C of the Yellow Group).

*Filaments.*—Size — Highly variable in length, approximately 9 to 16 mm. Color (RHS2001) — White (approximately 155A, 155B, 155C, and 155D of the White Group) and darkening with advanced maturity.

*Pistil.*—General — Generally taller or equal in height relative to the general anther height. The anthers and pistils are generally equal to or slightly taller than the petals. Length — Approximately 15 to 16 mm, including the ovary. Color (RHS2001) — Considered a light yellow-green when young (approximately 1C and 1D of the Green-Yellow Group) and becoming slightly darker with advancing senescence.

*Surface Texture.*—Is generally glabrous.

Fruit:

*Maturity when described.*—The present variety of fruit is described, as it would be found in its firm ripe condition at full commercial maturity. Under the ecological conditions prevailing in the medium chill zone of Texas it would be ripe in mid-May. The average ripe date at Pleasanton, Somerville and Fairfield experimental plots were May 10$^{th}$, May 9$^{th}$, and May 12$^{th}$ ,respectively.

*Size.*—General — Medium to medium large for the season and considered uniform. Average Cheek Diameter — Approximately 50 to 53 mm. Average Suture Diameter — Approximately 52 to 54 mm. Average Axial Diameter — Approximately 45 to 50 mm.

*Fruit Form.*—Generally considered oblate with unequal halves. Occasionally the fruit exhibits less symmetry when comparing the suture height with the line opposite the suture. The fruit is generally uniform in symmetry when viewed from the apical aspect.

*Fruit Suture.*—Generally, the suture appears as a thin line that extends from the base to the apex, and appears deeper at the apex, forming a shallow basin at the apical point. No apparent callusing or stitching exists along the suture line. Fruit suture depth at the midpoint is less than 1 mm. Color — Maroon, 59A of the Red-Purple Group and N186C, 187A and 187B of the Greyed — Purple Group.

*Ventral Surface.*—Form-Considered uniform.

*Stem Cavity.*—Width — Approximately 13 to 15 mm. Length — Approximately 16 to 21 mm. Depth — Approximately 5 to 8 mm.

*Fruit Base.*—Flat.

*Fruit Apex.*—Flat.

*Fruit Stem.*—Length — 7 to 8 mm. Thickness — 2 to 3 mm. Color — Light green, from 138C, 138D, 139D and 141D of the Green Group to 144C and 144D of the Yellow-Green Group.

*Fruit Skin.*—Generally considered medium or average in thickness. Surface Texture — Glabrous. Skin Acidity — Considered neutral. Tenacious to Flesh — Yes at commercial maturity. Tendency to Crack — Not observed. Skin Color — Generally-Variable, with approximately 80-90% of the fruit surface covered with an attractive maroon blush. Blush Color (RHS2001) — Maroon, 59A and 60A of the Red-Purple Group and 183A, 183B, 185A, N186C, 187A and 187B of the Greyed-Purple Group. Skin Ground Color (RHS2001) — Ivory, 2D, 4D and 11D of the Yellow Group, 155A, 155B, 155C, and 155D of the White Group and 158D of the Yellow-White Group.

*Flesh Color* (*RHS*2001).—White with maroon, approximately (RHS 2001) 58A, 59C, 60A, 60B and 61B of the Red-Purple Group, 187D of the Greyed-Purple Group and (R.H.S. Mini Colour Chart, 2005) N999D of the White Group. The maroon flesh color was medium to strong near the skin and weak to medium centrally and near the stone.

*Flesh Fibers.*—These fibers are present throughout the flesh.

*Stone Cavity Color* (*RHS*2001).—Tan, 161A and 161B of the Greyed-Yellow Group and 164B, 164C and 165C of the Greyed-Orange Group.

*Flesh Texture.*—Generally, the flesh is considered firm and fine at commercial maturity. Ripening-Generally the fruit of the present variety ripens evenly.

*Flavor.*—Considered very sweet (average Brix 12.6) with rich subacid flavor.

Stone:

*Attachment.*—Clingstone at commercial maturity.

*Stone Size.*—Length — Approximately 25 to 30 mm. Width — Approximately 16 to 18 mm. Thickness — Approximately 12 to 15 mm.

*Fibers.*—No fibers present.

*Stone Form.*—Elliptical.

*Stone Base Angle.*—The stone is narrow to medium.

*Hilum.*—The hilum is less than 1 mm wide.

*Stone Apex Angle.*—Narrow to medium.

*Stone Shape.*—Elongated to very elongated.

*Stone Surface.*—Surface Texture — Consists of single pits, rosettes of pits, chains of pits and pit grooves. Ridges — Numerous fine ridges are present basally and converge towards the base of the stone.

*Ventral Edge.*—Small to medium.

*Dorsal Edge.*—Shape-Grooved and having moderately rough edges.

*Stone Color* (*RHS*2001).—The color of the dry stone is tan (164B, 164C and 165D of the Greyed-Yellow Group). The color of the inside surface of the endocarp is primarily tan (158A of the Yellow-White Group and 164D and 165D of the Greyed-Orange Group.)

*Tendency to Split.*—Splitting is uncommon.

*Kernel.*—The elliptical kernel fills the endocarp at harvest and measures approximately 3-4 mm in thickness, 7-8 mm in width, and 15-16 mm in length. The color of the fresh kernel is a light brown with dark brown veins. Mainly, 161A, 161B, 161C, and 161D of the Greyed-Yellow Group and 163A, 164A, 164B, 164C, 164D, 165A, 165B, 165C and 165D of the Greyed-Orange Group. When dried the shriveled kernels measure approximately 2 mm in thickness, 5 mm in width, and 12-13 mm in length. The colors of the shriveled kernels are primarily light brown, 165B and 165C of the Greyed-Orange Group and N199D of the Grey-Brown Group.

*Use.*—The subject variety, 'TX2B444LWN', is considered to be a medium chill nectarine tree of early-season maturity, which produces subacid, white-fleshed, nectarine fruit which are very firm, with a 80-90% maroon blush with an ivory ground color, and which are useful for fresh fruit market.

*Keeping Quality.*—Average. Retains firmness and flavor after 14 days of refrigeration at 4-5° C.

*Resistance to Insects and Disease.*—Moderately susceptible to bacterial leaf spot (*Xanthamonas campestris* cv. *pruni*) similar to that seen in the cultivar 'TexKing'. Otherwise, no atypical resistances/susceptibilities were noted under normal cultural practices to date.

*Shipping Quality.*—Average. Fruit does not develop internal breakdown and retains good firmness and eating quality after 14 days of refrigeration at 4-5° C.

Although the new variety of nectarine tree possesses the described characteristics when grown under the ecological conditions prevailing in the medium chill zone of Texas in Pleasanton, Somerville and Fairfield, it will be understood that variations of the usual magnitude and characteristics incident to the changes in growing conditions, fertilization, pruning, and pest control are to be expected.

What is claimed is:

1. A new and distinct variety of nectarine tree named 'TX2B444LWN', as illustrated and described herein.

* * * * *